United States Patent [19]

Blay

[11] 3,983,208

[45] Sept. 28, 1976

[54] RECOVERY OF VANADIUM AND COPPER CATALYST METALS USING KETONES

[75] Inventor: Jorge A. Blay, Corpus Christi, Tex.

[73] Assignee: Celanese Corporation, New York, N.Y.

[22] Filed: Jan. 27, 1975

[21] Appl. No.: 544,158

[52] U.S. Cl. .................................... 423/27; 423/34; 423/64; 423/65; 423/68; 260/531 R; 260/537 P

[51] Int. Cl.² .................... C01G 3/00; C01G 31/00; C07C 55/14

[58] Field of Search .................. 423/23, 42, 63, 64, 423/65, 27, 34; 252/411, 413; 260/531 R, 537 P

[56] References Cited

UNITED STATES PATENTS

| | | | |
|---|---|---|---|
| 2,791,566 | 5/1957 | Jeffers | 252/413 X |
| 2,840,607 | 6/1958 | Attane et al. | 260/537 P |
| 2,971,010 | 2/1961 | Gilby et al. | 260/537 P |
| 2,980,720 | 4/1961 | Brown et al. | 260/537 X |
| 3,290,369 | 12/1966 | Bonfield et al. | 260/537 P |
| 3,459,512 | 8/1969 | Connolly et al. | 260/537 P |
| 3,818,081 | 6/1974 | Adamek | 260/537 P |

*Primary Examiner*—Oscar R. Vertiz
*Assistant Examiner*—Brian E. Hearn
*Attorney, Agent, or Firm*—Stewart N. Rice; Ralph M. Pritchett

[57] ABSTRACT

An aqueous nitric acid solution derived from an adipic acid process containing copper and vanadium catalyst values and alkyl dicarboxylic acids is treated to remove the nitric acid and water therefrom so as to obtain a substantially dry, molten-type residue. This residue is mixed with a dialkyl ketone solvent which dissolves the dicarboxylic acids and leaves the catalyst metal values as solids.

7 Claims, No Drawings

RECOVERY OF VANADIUM AND COPPER CATALYST METALS USING KETONES

BACKGROUND OF THE INVENTION

In the production of adipic acid by the liquid phase nitric acid oxidation of cyclohexanol and/or cyclohexanone in the presence of a copper-vanadium catalyst there generally results a purge waste stream containing valuable copper and vanadium ions therein of which recovery is desired if the process is to operate economically. These purge waste streams are generally derived from the mother liquor of one or more crystallizations involved in the recovery of the adipic acid and the necessity for purging arises because of the buildup of other dibasic acids such as succinic acid and glutaric acid. It is obvious that in view of the value of such catalyst metals, recovery of them from the purge waste stream is desirable before discarding same.

The basic process for the nitric acid oxidation of cyclohexanol and/or cyclohexanone in the presence of a copper-vanadium catalyst is well known in the prior art. The feed mixture utilized in most industrial processes is a mixture of cyclohexanone and cyclohexanol derived from the air oxidation of cyclohexane although some processes utilize only cyclohexanol or only cyclohexanone as a feed to the nitric acid oxidation. The cyclohexanol and/or cyclohexane is generally mixed with from 5 to 40 times its weight of an aqueous nitric acid solution, the nitric acid solution being generally of a concentration of 35 to 65% by weight, and there is also added the metal catalyst. Usually the copper and vanadium are added as ammonium metavandate and copper turnings, the total amount of catalyst usually being about 0.05 to 1.0% by weight of the reaction mixture. The liquid phase nitric acid oxidation is generally conducted at temperatures within the range of about 55°C to 100°C pressures within the range of about 1 to 5 atmospheres absolute.

There is produced in the nitric acid oxidation a liquid reaction product comprising the adipic acid and which also contains succinic acid, glutaric acid, nitric acid, water and the copper and vanadium catalyst values. Adipic acid crystals are recovered from the liquid reaction product by crystallization techniques, there resulting a mother liquor which comprises an aqueous nitric acid solution containing copper and vanadium values as well as dibasic carboxylic acids (mainly glutaric and succinic acids although some unrecovered adipic acid may also be present). A portion of this mother liquor may be and is generally recycled to the nitric acid oxidation reactor although a portion must be removed or purged to prevent buildup of the succinic and glutaric acid impurities, the portion removed or purged being the above-mentioned purge waste streams. The recovery of the adipic acid by crystallization is well known and such may be accomplished by one or more crystallization stages and may include effecting a removal of some nitric acid and water and re-dilution between crystallization steps.

Various methods have been developed for recovery of the copper and vanadium values from these purge waste streams as may be seen from U.S. Pat. Nos. 3,106,450; 3,186,952; 3,463,740; and 3,554,692. Also see British Patent Specifications 980762 and 956403. Even though various means have been derived for treating these purge waste streams so as to recover the catalyst values and other valuable components thereof, since the economic practicality of a given process often depends on a relatively narrow margin, research is constantly under way for a new and useful process for accomplishing the desired results.

It is thus an object of the present invention to provide a new and useful method for treating the above-described purge waste streams derived from an adipic acid process so as to recover valuable components thereof. It is a particular object of the present invention to provide a process for treating such purge waste streams so as to recover the copper and vanadium values therein. Additional objects will become apparent from the following description of the present invention.

SUMMARY

The foregoing and other objects are accomplished by the present invention which in one of its aspects is a process for the recovery of catalyst metal values from an aqueous nitric acid solution containing said catalyst metal values as well as $C_4$ to $C_6$ alkyl dicarboxylic acids, said aqueous nitric acid solution being derived from the crystallization zone of a process wherein cyclohexanol and/or cyclohexanone are oxidized in the liquid phase by nitric acid oxidation in the presence of catalyst metals corresponding to said catalyst metal values to produce a reaction product comprising adipic acid, and the adipic acid product recovered by crystallization in said crystallization zone, comprising:

a. treating said aqueous nitric acid solution to remove substantially all of the nitric acid and water therefrom and obtain a substantially dry, molten-type residue comprising said dicarboxylic acids and said catalyst metal values;

b. intimately mixing said residue with an amount of a liquid dialkyl ketone solvent sufficient to dissolve the said dicarboxylic acids in said residue so as to form a liquid-solid suspension, each alkyl group of said dialkyl ketone being of from one to four carbon atoms, the liquid phase of said liquid-solid suspension comprising a solution of said dicarboxylic acids in the said ketone solvent and the solid phase of said liquid-solid suspension comprising said catalyst metal values; and c. treating said liquid-solid suspension to separate said solid phase comprising said catalyst metal values from said liquid phase thereof.

In the following description and in the claims, all parts and percentages are by weight unless otherwise specified.

DETAILED DESCRIPTION OF THE INVENTION

According to the present invention, an aqueous nitric acid solution (that is the mother liquor or a derivative thereof) derived from the recovery of adipic acid by crystallization will first be concentrated and then mixed with a dialkyl ketone solvent. The exact makeup of such an aqueous nitric acid solution will depend on such factors as the crystallization procedure utilized, composition of the feed to the nitric acid oxidation and the like, although typically will contain by weight from about 10 to 35% nitric acid, 10 to 25% lower alkyl dicarboxylic acids (e.g. 5 to 15% glutaric, 1 to 10% succinic, and 1 to 10% adipic), 0.1 to 1.0% copper and 0.01 to 0.1% vanadium, the remainder being substantially water.

The first step in treating the aqueous nitric acid solution according to the invention is to concentrate such by removal of nitric acid and water and form a substantially dry molten-type residue containing the metal catalyst values and which will also contain the dibasic acids which were present in the aqueous nitric acid solution. The removal of the water and nitric acid is preferably effected by using a falling film evaporator or a wiped film evaporator although distillation techniques can be utilized. Water and nitric acid form a high boiling azeotrope of about seventy percent nitric acid and thirty percent water which has a boiling point of about 122°C at atmospheric pressure. Due to this azeotrope, when concentration of the solution begins only water will be initially removed until the ratio of nitric acid to water in the remaining liquid corresponds to the azeotropic composition, at which time the azeotrope will come off. The solution should be concentrated to such an extent that the content of the substantially dry molten-type residue contains less than about 0.7% by weight nitric acid and preferably less than about 0.3% by weight nitric acid. Since the nitric acid and water left in the substantially dry molten-type residue will correspond to the azeotropic composition, the amount of water present will be less than about 0.3% by weight, preferably less than about 0.13% by weight. If too much nitric acid remains in the residue, then the catalyst values will unduly solubilize when the residue is mixed with the dialkyl ketone.

The next step of the invention is to mix the substantially dry, molten-type residue so obtained with a dialkyl ketone solvent in which the alkyl dicarboxylic acids are soluble and the catalyst metal values are insoluble. For this purpose a dialkyl ketone having from one to four carbon atoms in each alkyl group is suitable. It is, however, preferred to utilize only those ketones wherein each alkyl group contains no more than two carbon atoms, that is acetone (which is especially preferred), methyl ethyl ketone or diethyl ketone. Other suitable ketones include diisopropyl ketone and dibutyl ketone. The mixing of the residue and ketone solvent can take place in conventional mixing equipment such as an open stirred vessel. The temperature during mixing is not critical although the temperature should obviously not be so high as to cause boiling or so low as to cause solidification. Suitable mixing temperatures are in the range of about 15° to 60°C, preferably about 40° to 56°C, when the ketone is acetone used at atmospheric pressure.

The amount of ketone solvent required to be mixed with the substantially dry residue will vary according to such factors as mixing temperature, the particular ketone used, and composition of the molten-type residue, the latter being a factor since some of the alkyl dicarboxylic acids in the residue are more soluble than others. Only an amount of ketone sufficient to dissolve, at the mixing temperature, the alkyl dicarboxylic acids in the residue is needed although an excess is preferably utilized, for example, from 2 to 15 times the amount necessary for dissolution of the dicarboxylic acids. Greater amounts may be utilized but such will usually be uneconomical. Generally an amount of ketone which is from 2 to 4 times the weight of the substantially dry, molten-type residue will be used.

Upon mixing the ketone with the residue, a liquid-solid slurry or suspension will result. The liquid phase of the liquid-solid suspension will comprise mainly a solution of the alkyl dicarboxylic acids in the ketone solvent, although a small amount of the catalyst metal values will also be present in solution as will be small amounts of water and nitric acid. The higher the nitric acid content of the residue the more catalyst that will be solubilized, and, it is for this reason that the nitric acid content be kept low as economically feasible. The solid phase of the suspension will contain the catalyst metal values such being present generally in the form of copper oxides, copper salts of dicarboxylic acids, cupric polyvandate and hydrated vanadium pentoxide. The solid phase of the suspension may easily be separated from the liquid phase by conventional means including filtration and centrifugation, although filtration is the preferred means.

Separation can be aided by adding to the suspension enough ammonia or ammonium hydroxide to neutralize from about 0.5 to 3% of, preferably about 1% of, the alkyl dicarboxylic acids present. This apparently results in formation of an ammonium glutarate salt which is hydrophillic and aids quick coagulation. The reason for this is that the hydrophillic molecules have very low solubility in the ketone solvent but do attract any water present so as to form an aqueous phase which wets the catalyst particles and causes coagulation. Instead of adding ammonia or ammonium hydroxide, a hydrophillic ammonium salt may be added such as ammonium salts of adipic acid, acetic acid or propionic acid. The addition of non-hydrophillic ammonium salts such as ammonium nitrate is not desirable. An even greater recovery of the catalyst values can be accomplished by adding a small amount of an aqueous solution of a hydrophillic salt (for example a 50% aqueous solution of ammonium acetate) to the liquid phase of the suspension after the initial separation thereof from the solid phase. Thus addition of one part of a 50% aqueous solution of ammonium acetate to 100 parts of the liquid phase followed by vigorous agitation will result in practically complete extraction of the catalyst values from the liquid phase.

The catalyst metal values recovered as the solid phase of the liquid-solid suspension may be utilized as desired. It will generally be most feasible to redissolve these catalyst metal values in nitric acid and recycle them to the nitric acid oxidation of the cyclohexanol and/or cyclohexanone. Various means may be utilized to recover the components of the liquid phase of the suspension, the most simple method being to pass the liquid phase to a non-cooling evaporator to obtain the ketone solvent and also obtain a second molten-type residue comprising mainly the alkyl dicarboxylic acids. The ketone solvent may be recycled and this second molten-type residue may be discarded or used for plasticizers or the like.

The recommended manner of treating the liquid phase of the liquid-solid suspension is however to first subject it to evaporative cooling under vacuum to effect crystallization of alkyl dicarboxylic acids substantially free of the catalyst metals. This may be accomplished in a falling film or wiped film evaporator. The crystalline alkyl dicaboxylic acids may be utilized as desired and the mother liquor from this evaporative cooling may then be passed to a non-cooling evaporator to recover the ketone solvent and also produce a second molten-type residue. This second molten-type residue will contain substantially all of the catalyst metals which were solubilized in the ketone solvent and also contain alkyl dicarboxylic acids. The ratio of glutaric acids will be higher in this second molten-type residue than in the liquid phase separated from the liquid-solid suspension due to the relatively high solubility of glutaric acid. This second molten-type residue may be recycled to the beginning of the process to be mixed with the purge waste stream derived from the adipic acid process prior to its being subjected to the evaporative cooling. The increased ratio of glutaric acid to the other dicarboxylic acids in this second molten-type residue is beneficial when added to the purge waste stream in that the substantially dry residue produced in the evaporative cooling of the purge waste stream is more flowable, thus resulting in improved operation of the falling or wiped film evaporator.

EXAMPLE I

A purge waste acid stream derived from the recovery of adipic acid by crystallization in a process wherein adipic acid was produced by the liquid phase oxidation of a cyclohexanol/cyclohexanone mixture using a copper-vanadium catalyst was treated according to the present invention. The purge waste acid stream contained about 4.5% succinic acid, 9.0% glutaric acid, 2.9% adipic acid, 0.8% copper, 0.13% vanadium and 23.8% nitric acid, the remainder comprising mainly water. The purge waste acid stream was passed to a wiped film evaporator to obtain a substantially dry molten-type residue containing less than 0.2% nitric acid. The molten-type residue which had a temperature of 130°C was allowed to cool to about 85°C and then mixed with twice its weight of room temperature acetone to result in a suspension having a temperature of about 50°C. The dicarboxylic acids were completely solubilized. In order to aid coagulation, enough concentrated ammonium hydroxide was then added to neutralize 1% of the dicarboxylic acids and the suspension filtered under pressure. The filter cake was dried and analyzed and found to contain about 97.6% of the metal values in the charged purge waste acid.

EXAMPLE II

The experiment of Example I was repeated except that the filtrate was evaporatively cooled to −20°C under vacuum to effect crystallization of dibasic carboxylic acids which were then separated by a second filtration. The mother liquor from the second filtration was evaporated to substantial dryness to obtain a second molten-type residue which was then recycled to the beginning of the process and mixed with the purge waste acid. Operation utilizing this recycle resulted in the recovery of another 2.2% of the catalyst metals or a 99.8% overall recovery.

The embodiments of the invention in which an exclusive property or privilege is claimed and defined as follows:

1. A process for the separation of copper and vanadium catalyst metal values from an aqueous nitric acid solution containing said catalyst metal values as well as $C_4$ to $C_6$ alkyl dicarboxylic acids, said aqueous nitric acid solution being derived from the crystallization zone of a process wherein cyclohexanol and/or cyclohexanone are oxidized in the liquid phase by nitric acid oxidation in the presence of catalyst metals corresponding to said catalyst metal values to produce a reaction product comprising adipic acid, and the adipic acid product recovered by crystallization in said crystallization zone, comprising:

a. treating said aqueous nitric acid solution to remove substantially all of the nitric acid and water therefrom and obtain a substantially dry, molten-type residue comprising said dicarboxylic acids and said catalyst metal values;

b. intimately mixing said residue with an amount of a liquid dialkyl ketone solvent sufficient to dissolve the said dicarboxylic acids in said residue so as to form a liquid-solid suspension, each alkyl group of said dialkyl ketone being of from one to four carbon atoms, the liquid phase of said liquid-solid suspension comprising a solution of said dicarboxylic acids in the said ketone solvent and the solid phase of said liquid-solid suspension comprising said catalyst metal values;

c. adding to said liquid-solid suspension an amount of ammonia or ammonium hydroxide sufficient to neutralize from about 0.5 to 3% of the dicarboxylic acids contained therein; and d. separating said solid phase comprising said catalyst metal values from said liquid-solid suspension.

2. The process of claim 1 wherein the amount of nitric acid removed from said aqueous nitric acid solution is sufficient to reduce the nitric acid content of said residue to below 0.3% by weight thereof.

3. The process of claim 2 wherein said dialkyl ketone is acetone.

4. The process of claim 2 wherein each alkyl group of said dialkyl ketone contains no more than two carbon atoms, and wherein the amount of said ketone solvent mixed with said residue is from about 2 to 15 times the weight of said residue.

5. The process of claim 4 wherein the mixing of said residue with said ketone solvent is at a temperature within the range of 15° to 60°C. and wherein said ketone is acetone.

6. The process of claim 1 wherein each alkyl group of said dialkyl ketone contains no more than two carbon atoms.

7. The process of claim 1 wherein the amount of said ketone solvent mixed with said residue is from about 2 to 15 times the weight of said residue.

* * * * *